(12) United States Patent
Hassanzadeh

(10) Patent No.: US 10,391,249 B2
(45) Date of Patent: Aug. 27, 2019

(54) DROPPER SYRINGE APPARATUS

(71) Applicant: Belal Hassanzadeh, Tabriz (IR)

(72) Inventor: Belal Hassanzadeh, Tabriz (IR)

( * ) Notice: Subject to any disclaimer, the term of this patent is extended or adjusted under 35 U.S.C. 154(b) by 267 days.

(21) Appl. No.: 15/642,240

(22) Filed: Jul. 5, 2017

(65) Prior Publication Data

US 2018/0214638 A1 Aug. 2, 2018

(30) Foreign Application Priority Data

Jan. 30, 2017 (IR) .................... 13955014000301383

(51) Int. Cl.
| | | |
|---|---|---|
| *A61M 5/31* | (2006.01) | |
| *A61F 9/00* | (2006.01) | |
| *A61J 7/00* | (2006.01) | |
| *A61M 5/32* | (2006.01) | |
| *B01L 3/02* | (2006.01) | |
| *A61M 5/315* | (2006.01) | |
| *A61D 7/00* | (2006.01) | |
| *A61M 5/19* | (2006.01) | |

(52) U.S. Cl.
CPC ......... *A61M 5/3137* (2013.01); *A61F 9/0008* (2013.01); *A61J 7/0053* (2013.01); *A61M 5/31531* (2013.01); *A61M 5/3202* (2013.01); *B01L 3/0217* (2013.01); *B01L 3/0241* (2013.01); *A61D 7/00* (2013.01); *A61M 5/19* (2013.01); *A61M 2005/3126* (2013.01); *B01L 2200/087* (2013.01); *B01L 2300/0672* (2013.01); *B01L 2300/0832* (2013.01); *B01L 2300/123* (2013.01); *B01L 2400/0478* (2013.01)

(58) Field of Classification Search
CPC .............. A61M 5/3137; A61M 5/3202; A61M 2005/3126; A61M 5/31531; A61J 7/0053; A61D 7/00; A61F 9/0008; B01L 3/0217; B03L 3/0241
See application file for complete search history.

(56) References Cited

U.S. PATENT DOCUMENTS

| | | | | |
|---|---|---|---|---|
| 3,464,412 A | * | 9/1969 | Boris ................. | A61B 5/15003 222/386 |
| 5,383,906 A | * | 1/1995 | Burchett ............... | A61J 7/0046 222/133 |
| 5,775,546 A | * | 7/1998 | Buehler .................. | B01L 3/021 222/209 |
| 6,238,120 B1 | * | 5/2001 | Mark ...................... | A45D 19/02 401/134 |

(Continued)

*Primary Examiner* — Theodore J Stigell

(57) ABSTRACT

A dropper syringe apparatus includes a cylindrical barrel, a plunger assembly, and a needle. The cylindrical barrel storing the fluid includes a flanged first opening and a second opening. The plunger assembly, inserted into the cylindrical barrel, includes a plunger shaft and a flexible hollow bulb. The plunger shaft includes a flanged upper end, a lower end, and a central lumen. The plunger shaft moves in an upward and a downward direction within the cylindrical barrel. The central lumen extends from the lower to the flanged upper end of the plunger shaft for accommodating the fluid. The flexible hollow bulb is fixedly attached to the flanged upper end and in fluid communication with the central lumen. An external force exerted on the flexible hollow bulb exerts a pressure on the fluid accommodated within the lumen. The needle draws or dispenses the fluid from or to the external body.

16 Claims, 9 Drawing Sheets

(56) References Cited

U.S. PATENT DOCUMENTS

| | | | | |
|---|---|---|---|---|
| 9,333,299 B2* | 5/2016 | Kanazawa | ............ | A61M 5/284 |
| 2003/0139706 A1* | 7/2003 | Gray | ................... | A61M 5/3135 |
| | | | | 604/199 |
| 2006/0253087 A1* | 11/2006 | Vlodaver | ................ | A61F 11/00 |
| | | | | 604/275 |

* cited by examiner

DROPPER SYRINGE APPARATUS

BACKGROUND OF THE INVENTION

Every year, dozens of new medicines and medical compounds are produced to treat various diseases. Millions of liters of sterile fluids like eye drops, IV solutions, and others are produced each year for these purposes. Despite advances in the field of medical science, over the past years, little progress has been made in medication delivery methods. Each year, millions of dollars are spent to produce these types of medicines. Yet, wastage of medications because of inappropriate delivery systems is a growing problem. Beside consumers, insurance companies, health care organizations, and governmental agencies face economic losses because of the process of erratic dispensing of medications.

Nowadays, sterile fluids have medical, cosmetic, or laboratory applications, like ophthalmology medications, various saline compounds and other injectable or non-injectable solutions. Generally, containers or vials containing theses fluids have suitable dispensing mechanisms well appropriated for use. However, in some cases, external dispensing mechanisms or apparatuses particularly suited for a storage container are required to dispense stored liquids for different purposes. For example, saline intravenous (IV) solutions are usually packed in flexible plastic bags that are very appropriate for intravenous infusion, but in some cases, one may need to use some of these fluids to rinse an eye, feed a newborn or a pup, etc. Although, in operation rooms conditions arise that the personnel forced to draw out some fluid from a sealed vial and drop it one by one on the operation site.

In these conditions at the first step, you have to draw out some fluid from container and at the second step; you have to instill the fluid as drops on the target place. The first step could be done with a conventional syringe, but for second step, two choices exist and both have their own problems. The first choice is using the same syringe and the second is applying a bottle and a dropper. If you use the same syringe for instilling the fluid, it is necessary to carefully control the thumb pressure on the syringe plunger to prevent the syringe contents from suddenly splashing out. Fine dispensing of the sterile liquid from a conventional syringe is highly annoying and difficult to reproduce, and cannot be executed suitably by everybody. Often, therefore, larger quantities of the sterile liquid are dispensed to the target place than required. Additionally, if there is sudden movement of the target object, more of the sterile liquid is wasted.

Your second choice for this purpose is applying a couple of excess devices including a bottle and a dropper with rubber bulb. For maintaining the sterility of the fluid both of them should be sterile and keep from collision with anything. Although the main disadvantage of this choice is high probability of contamination, but imposing additional costs is its other disfavor.

A practical example of this problem: When you want to feed a newborn or a pup by dispensing small quantities of the sterile fluid. You can draw out some fluid by a conventional syringe, but you cannot use the same syringe to dispense the fluid as drops, because it is difficult to synchronize the dispensing device with random movement of a newborn or a pup and simultaneously finely dispense sterile fluid on the target object. In the above-mentioned scenario, many drops of the dispensed sterile fluid are wasted unnecessarily. Moreover, some of the dispensed drops may fall in the nostrils or eyes, which cause dire consequences.

In the case of ophthalmology medications and eye drops, the main problem is maintaining the sterility of the drop. A minor contact of the dropper tip to anything including the skin and lashes causing it to be non-sterile. Even highly efficient eye drop dispensing devices may become non-sterile due to a slight collision and whole of the dropper bottle should be discarded. Despite all the caution that people take, many of these bottles are thrown away daily. It is obvious that the collision between tip of the eyedropper bottle and the skin or lashes is not completely preventable. This is because of visual accommodation system of the human eyes, which permit focusing on both near and far objectives. The minimum distance that the human eye is able to see ranges from about 25 cm to 50 cm in most individuals over the age of 50. Considering the fact that the maximum appropriate distance between eye and dropper could not be more than 20-30 cm and the fact that the most people who have eye and vision problems are aged, the problem of aligning the dropper with the eye and the possibility of being unsterile is prevalent.

Another group of people who use plenty of eye drops is individuals who have had an eye operation or use an artificial medical or cosmetic eye lenses. Regardless of age, this group of people usually has to apply eye drops by themselves. Given that sterility is a very important factor for this group, they usually throw away a large number of eye drop dispensers due to being unsterile. Therefore, in the case of ophthalmology drops if the medication was in a sealed vial and the person was able to draw out a few drops and instill it in the eye, it would not be necessary to throw away the entire drug with a slight collision.

Existing devices do not allow users to draw out sterile liquid from the plastic bag or a sealed vial and dispense the sterile liquid as drops on a target place. Although some irrigation syringes are available in market, but there is a need in the marketplace for an apparatus or device, which allows a user to draw and dispense sterile fluid and directly instill the fluid as drops on the target place, and could be used as an injection syringe. Furthermore, by using of such a device, ophthalmology medications, which are generally produced and sold in the form of sterile dropper bottles, could be presented in sealed vials.

Another group of people who use drop dispensers is laboratory technicians. Sometimes they need a few drops of a hazardous liquid with toxic fumes, for example, formaldehyde or glutaraldehyde, which is in a sealed vial. So, they are faced with problems of avoiding exposure to toxic fumes. According to the above explanation, it seems the best way to prevent wasting of the liquid and avoid toxic fumes is to separate the container and dropper. The container should be sealed and the dropper should be able to draw out the liquid without opening the container. Thus, there is also a need in the art for an apparatus or a device, which enables a user to draw out a few drops of the liquids and directly instill it in a beaker without exposure to toxic fumes.

In sum, there is a long felt but unresolved need for apparatus or device, which allows a user to draw and dispense sterile fluid and directly instill the fluid as drops on the target place, as well as also providing the functions of the injection syringe and the dropper. Moreover, there is a need for an inexpensive and disposable device to prevent wastage of ophthalmology drops. In this way, the ophthalmology drops will be presented in sealed vials and people will use the disposable cheap device to draw out few liquid from the vial and consequently instill it in their eyes. In this manner, if the dispensing device became unsterile the user will throw it away and preserve the remaining medication in the vial.

Furthermore, there is a need for an apparatus or device, which enables a user to draw out a few drops of the liquids and directly instill it in a beaker without exposure to toxic fumes.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The dropper syringe apparatus, disclosed herein, addresses the above-mentioned need for an apparatus or a device, which allows a user to draw and dispense sterile fluid and directly instill the fluid as drops on the target place. Moreover, the invention addresses the need for an apparatus or device, which prevents any dispensing part contacting the infected body part. Furthermore, the invention addresses the need for an apparatus or device, which enables a user to draw out a few drops of the liquids and directly instill it in a beaker without exposure to toxic fumes. The dropper syringe apparatus for drawing or dispensing fluid from or to an external body comprises a substantially cylindrical barrel, a plunger assembly, and a needle. The substantially cylindrical barrel comprises a first opening and a second opening. The second opening is smaller than the first opening. The first opening is flanged and the substantially cylindrical barrel is configured to store the fluid. The plunger assembly is configured to be inserted into the substantially cylindrical barrel.

The plunger assembly comprises a plunger shaft and a flexible hollow bulb. The plunger shaft comprises a flanged upper end, a lower end, and a central lumen. The plunger shaft is configured to move in an upward direction and a downward direction within the substantially cylindrical barrel. The central lumen extends from the lower end to the flanged upper end of the plunger shaft for accommodating the fluid. The flexible hollow bulb is fixedly attached to the flanged upper end of the plunger shaft.

The interior of the flexible hollow bulb is in fluid communication with the central lumen. Further, the flexible hollow bulb is configured to exert a pressure on the fluid accommodated within the central lumen based on an external force exerted on the flexible hollow bulb. The needle is detachably attached to a first hollow neck element extending from the second opening of the substantially cylindrical barrel. Additionally, the needle is configured to draw or dispense the fluid from or to the external body.

The present invention addresses the problems associated with drawing out a liquid and directly instilling it as one by one drops into the target place (eye, mouth, operation site, beaker, etc.) in a safe, easy, and precise manner with minimum waste. The dropper syringe apparatus has been designed as a combination of a syringe with a dropper in which the plunger shaft comprises a central lumen. The dropper syringe apparatus is used as an ordinary syringe for drawing out a sterile liquid from a sealed vial or plastic bag and then injecting it in someone's body. Alternately, the dropper syringe apparatus is used for drawing out a sterile liquid from a sealed vial and directly instilling it as drops on an eye, an ear, nostrils, an operation site, or into a mouth of a newborn or a pup.

When the flexible hollow bulb is manipulated by two fingers from two sides the inside air is drawn into the central lumen and exit from the other side as some drops through the syringe end hole. Subsequently, when the flexible hollow bulb is left relaxed, it expands again and sucks some air through the syringe end hole so the operator can repeat the dropping action. While the flexible hollow bulb is pressed from the top, the interior projection of the flexible hollow bulb will place in the opening of the dropper pipe and prevent the air to flux into the cavity of the substantially cylindrical barrel. Therefore, an intense pressure on top of the flexible hollow bulb will cause the plunger shaft to move forward and flux the fluid from the syringe end hole, and if the needle has been inserted in a body this process leads to the injection of the fluid within the substantially cylindrical barrel into the body.

A primary object of this invention is drawing out a sterile fluid and directly instilling it as drops one by one into an eye, an ear, or nostrils for therapeutic purposes. Another object of this invention is drawing out a sterile fluid and directly instilling it as drops one by one into the mouth of a newborn or a pup for feeding or therapeutic purposes. Another object of this invention is drawing out a hazardous chemical liquid and directly instilling it as drops one by one into a bottle or anywhere else needed for carrying out a chemical reaction in a lab.

One aspect of the present disclosure is a dropper syringe apparatus for drawing or dispensing fluid from or to an external body. The dropper syringe apparatus comprises (a) a substantially cylindrical barrel comprising a first opening and a second opening, the second opening smaller than the first opening, wherein the first opening is flanged as two symmetrical finger grips, and wherein the substantially cylindrical barrel is configured to store the fluid; (b) a plunger assembly configured to be inserted into the substantially cylindrical barrel, the plunger assembly comprising: (i) a plunger shaft comprising a flanged upper end, a lower end, and a central lumen, the plunger shaft configured to move in an upward direction and a downward direction within the substantially cylindrical barrel, wherein the central lumen extends from the lower end to the flanged upper end of the plunger shaft for accommodating the fluid; (ii) a flexible hollow bulb fixedly attached to the flanged upper end of the plunger shaft, wherein the interior of the flexible hollow bulb is in fluid communication with the central lumen, the flexible hollow bulb configured to exert a pressure on the fluid accommodated within the central lumen based on an external force exerted on the flexible hollow bulb; and (iii) a needle detachably attached to a first hollow neck element extending from the second opening of the substantially cylindrical barrel, the needle configured to draw or dispense the fluid from or to the external body.

In one embodiment, the dropper syringe apparatus further comprises a needle protector configured to house the needle and prevent contamination of the needle. In another embodiment, the needle is detached from the first hollow neck element and drops of the fluid are dispensed from the first hollow neck element based on the external force exerted on the flexible hollow bulb.

In one embodiment, the dropper syringe apparatus further comprises a second hollow neck element attached to the flanged upper end of the plunger shaft, the second hollow neck element housed within the flexible hollow bulb, wherein the second hollow neck element is in fluid communication with the central lumen of the plunger shaft and the flexible hollow bulb to transfer fluid between the central lumen and the flexible hollow bulb. In one embodiment, the flanged upper end of the plunger shaft is configured as a circular handle. In another embodiment, the substantially cylindrical barrel is of a transparent plastic material. In one embodiment, the flexible hollow bulb is of a rubber material. In another embodiment, the fluid is a sterile liquid. In one embodiment, the external body is one of a sealed vial storing sterile liquid, a body part of a human, and a body part of an animal.

Another aspect of the present disclosure is directed to a dropper syringe apparatus for drawing or dispensing fluid from or to an external body. The dropper syringe apparatus comprises (a) a substantially cylindrical barrel comprising a first opening and a second opening, the second opening smaller than the first opening, wherein the first opening is flanged as two symmetrical finger grips, and wherein the substantially cylindrical barrel is configured to store the fluid; (b) a plunger assembly configured to be inserted into the substantially cylindrical barrel, the plunger assembly comprising: (i) a plunger shaft comprising a flanged upper end, a lower end, and a central lumen, the plunger shaft configured to move in an upward direction and a downward direction within the substantially cylindrical barrel, wherein the central lumen extends from the lower end to the flanged upper end of the plunger shaft for accommodating the fluid; (ii) a second hollow neck element attached to the flanged upper end of the plunger shaft, wherein the second hollow neck element is in fluid communication with the central lumen of the plunger shaft and a flexible hollow bulb to transfer fluid between the central lumen and the flexible hollow bulb; (iii) the flexible hollow bulb fixedly attached to the flanged upper end of the plunger shaft, wherein the interior of the flexible hollow bulb houses the second hollow neck element, wherein the flexible hollow bulb is configured to exert a pressure on the fluid accommodated within the central lumen based on an external force exerted on the flexible hollow bulb; and (c) a needle detachably attached to a first hollow neck element extending from the second opening of the substantially cylindrical barrel, the needle housed in a needle protector, wherein the needle is configured to draw or dispense the fluid from or to the external body.

In one embodiment, the needle is detached from the first hollow neck element and drops of the fluid are dispensed from the first hollow neck element based on the external force exerted on the flexible hollow bulb. In one embodiment, the flanged upper end of the plunger shaft is configured as a circular handle piece. In another embodiment, the substantially cylindrical barrel is of a transparent plastic material. In one embodiment, the flexible hollow bulb is of a rubber material.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The present invention relates generally to the field of medical devices. More specifically, the present invention pertains to a dropper syringe apparatus for drawing out a sterile liquid from an external body and accurately dispensing the sterile liquid as drops. Additionally, the present invention is used for injecting a medicine, dropping ophthalmology medications into an eye, dropping liquid medications on the operation site in operation rooms, dropping liquid medications into an ear or nostril, dropping a sterile liquid into a mouth of a human or and an animal. Moreover, the present invention is capable of drawing out and dispensing hazardous chemical liquids anywhere, as required.

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and components disclosed herein.

FIG. 4B exemplarily illustrates an enlarged sectional view of a flexible hollow bulb shown in FIG. 4A.

DETAILED DESCRIPTION

A description of embodiments of the present invention will now be given with reference to the Figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
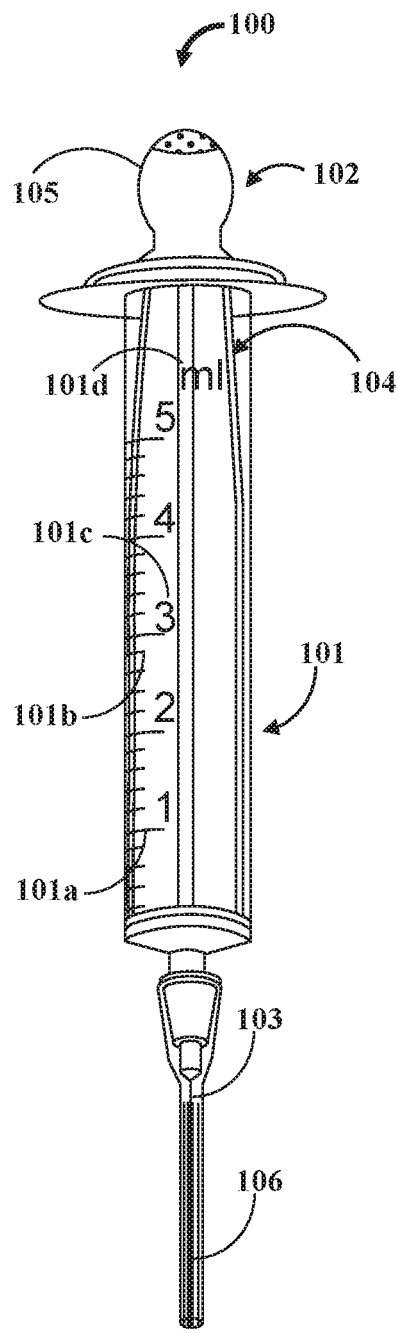
FIG. 1 exemplarily illustrates a perspective view of a dropper syringe apparatus.

FIG. 1 exemplarily illustrates a perspective view of a dropper syringe apparatus 100. Although the useable volume of the preferred embodiment of the dropper syringe apparatus 100 is about 5 milliliters, the dropper syringe apparatus 100 is produced in any appropriate volume ranging from about 0.1-10 milliliters. As used herein, the term "dropper syringe apparatus" is intended to designate a syringe, which is interchangeably used as a dropper or a syringe. The dropper syringe apparatus 100 for drawing or dispensing fluid from or to an external body comprises a substantially cylindrical barrel 101, a plunger assembly 102, and a needle 103.

As used herein, the term "substantially cylindrical" refers to the general geometric configuration of the barrel. In this regard, the barrel is also configurable as an oval, elliptical, or cuboidal barrel according to design or productivity requirements. The substantially cylindrical barrel 101 is configured to store the fluid, for example, a sterile liquid, a toxic chemical, a vaccine, etc. The plunger assembly 102 is configured to be inserted into the substantially cylindrical barrel 101. The plunger assembly 102 comprises a plunger shaft 104 and a flexible hollow bulb 105. In an embodiment, a needle protector 106 is provided to house the needle 103 of the dropper syringe apparatus 100. The needle protector 106 prevents the needle 103 from coming into contact with external contaminants.

As exemplarily illustrated in FIG. 1, a dropper syringe 100 includes a substantially cylindrical barrel 101 and a plunger shaft 104 movably disposed within a cylindrical-shaped internal volume of the substantially cylindrical barrel 101. In an embodiment, the substantially cylindrical barrel 101 is made of a transparent material. Consequently, the plunger shaft 104 is visible when the plunger shaft 104 is positioned in the substantially cylindrical barrel 101.

The graduation marks are printed along the external surface of the substantially cylindrical barrel 101, including major lines 101a, minor lines 101b, numbers 101c, and the symbol of milliliter 101d. In an embodiment, the substantially cylindrical barrel 101 is configured as a wide flange at an end, which is formed as two symmetrical finger grips. All parts of the dropper syringe apparatus 100 are made of plastic, except the needle 103 and the flexible hollow bulb 105. In an embodiment, the needle 103 is made of metal and the flexible hollow bulb 105 is always made of resilient rubber. The substantially cylindrical barrel 101 is made of transparent plastic.

Figure 2:
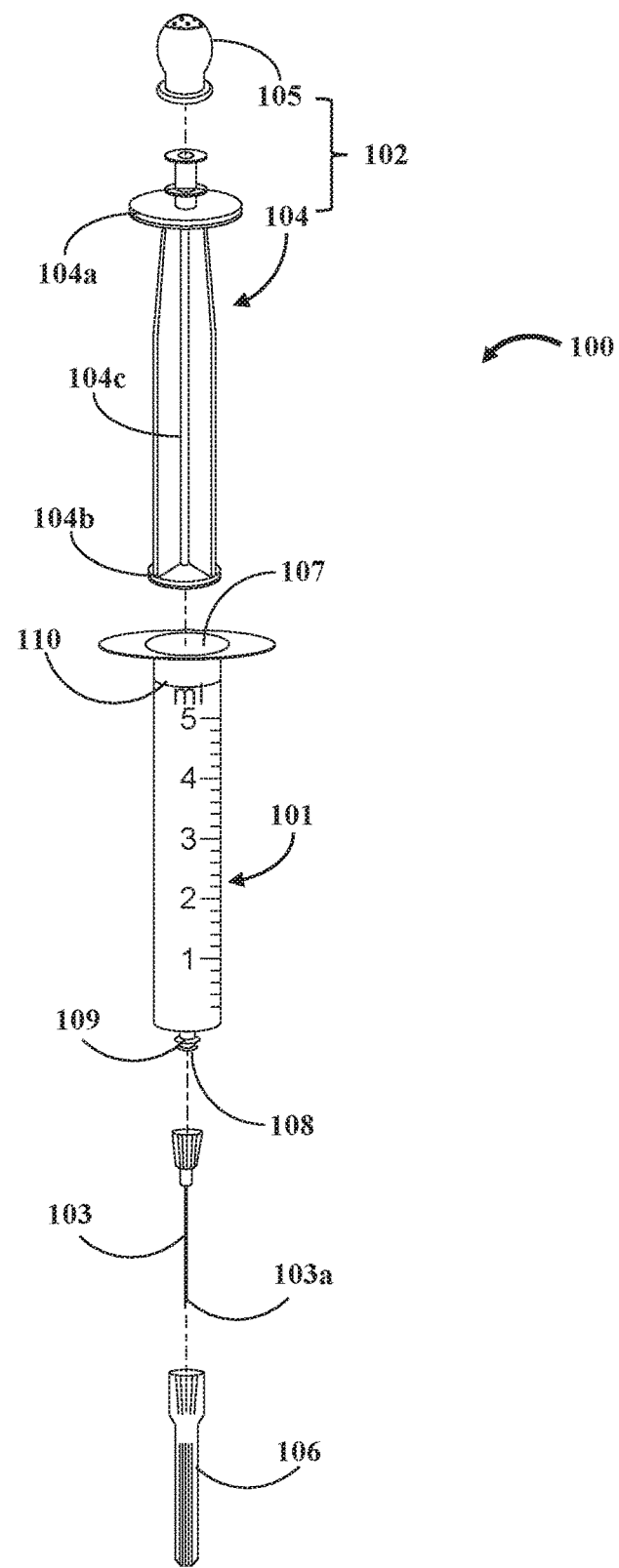
FIG. 2 exemplarily illustrates an exploded view of a dropper syringe apparatus.

FIG. 2 exemplarily illustrates an exploded view of a dropper syringe apparatus 100. As disclosed in the detailed description of FIG. 1, the dropper syringe apparatus 100 comprises a substantially cylindrical barrel 101, a plunger assembly 102, a needle 103, and a flexible hollow bulb 105. The substantially cylindrical barrel 101 comprises a first opening 107 and a second opening 108. The second opening 108 is configured to be smaller than the first opening 107. The first opening 107 is flanged and the substantially cylindrical barrel 101 is configured to store the fluid.

Adjacent to the first opening 107 of the substantially cylindrical barrel 101, the inner surface of the substantially cylindrical barrel 101 has a delicate prominent line, which works as a backstop line 110. The backstop line 110 prevents dislocation of the plunger shaft 104 while retracting. The first opening 107 of the substantially cylindrical barrel 101 is open and adapted for receiving the plunger shaft 104. The plunger shaft 104 comprises a flanged upper end 104a, a lower end 104b, and a central lumen 104c. The plunger shaft 104 is configured to move in an upward direction and a downward direction within the substantially cylindrical barrel 101.

The central lumen 104c extends from the lower end 104b to the flanged upper end 104a of the plunger shaft 104 for accommodating the fluid, for example, sterile liquid, toxic chemical fluids, etc. The flanged upper end 104a is only used for retracting the plunger shaft 104 not pushing the plunger shaft 104. The flexible hollow bulb 105 is fixedly attached to the flanged upper end 104a of the plunger shaft 104. In an embodiment, the external surface of the top/tip portion of the flexible hollow bulb 105 is made of a spherical coarse material to prevent slipping the thumb while pushing the plunger shaft 104.

The interior of the flexible hollow bulb 105 is in fluid communication with the central lumen 104c. The flexible hollow bulb 105 is configured to exert a pressure on the fluid accommodated within the central lumen 104c based on an external force exerted on the flexible hollow bulb 105. The needle 103 is detachably attached to a first hollow neck element 109 extending from the second opening 108 of the substantially cylindrical barrel 101. The needle 103 is configured to draw or dispense the fluid from or to the external body via the needle hole 103a.

Figure 3A:
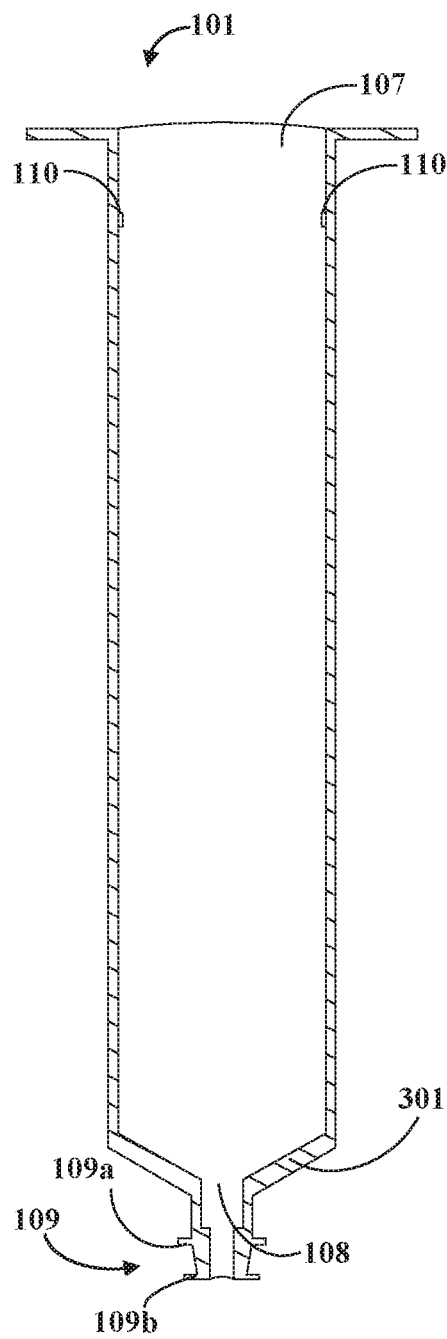
FIG. 3A exemplarily illustrates a sectional view of a barrel of a dropper syringe apparatus.

FIG. 3A exemplarily illustrates a sectional view of a substantially cylindrical barrel 101 of a dropper syringe apparatus 100. The substantially cylindrical barrel 101 comprises a first opening 107 and a second opening 108. In the preferred embodiment, the second opening 108 is smaller than the first opening 107. Further, the first opening 107 is flanged as two symmetrical finger grips and the substantially cylindrical barrel 101 is configured to store the fluid. The wall 301 distal to the first opening 107 of the substantially cylindrical barrel 101 has a conical shape which completely fits with the lower end 104b of the plunger shaft 104 exemplarily illustrated in FIG. 2. On the external surface of the wall 301, the first hollow neck element 109 extends from the second opening 108.

In an embodiment, the first hollow neck element 109 comprises an upper flange 109a and a lower flange 109b. The upper flange 109a is a bit larger than the lower flange 109b of the first hollow neck element 109. The lower flange 109b helps to ease flow of the falling drops. The drops slide on the surface of the lower flange 109b and easily fell down. This causes each drop not to attach with others and drops fall down one by one. The upper flange 109a, which is a bit larger, has no function in dropping action but it is involved in latching and fastening of the needle on the dropper syringe apparatus 100. Further, the pyramidal or trapezoidal shape of the needle plastic hub, exemplarily illustrated in FIG. 3C, is configured to completely house both the upper flange 109a and the lower flange 109b of the dropper syringe apparatus 100 enabling latching of the needle on the dropper syringe apparatus 100.

Figure 3B:
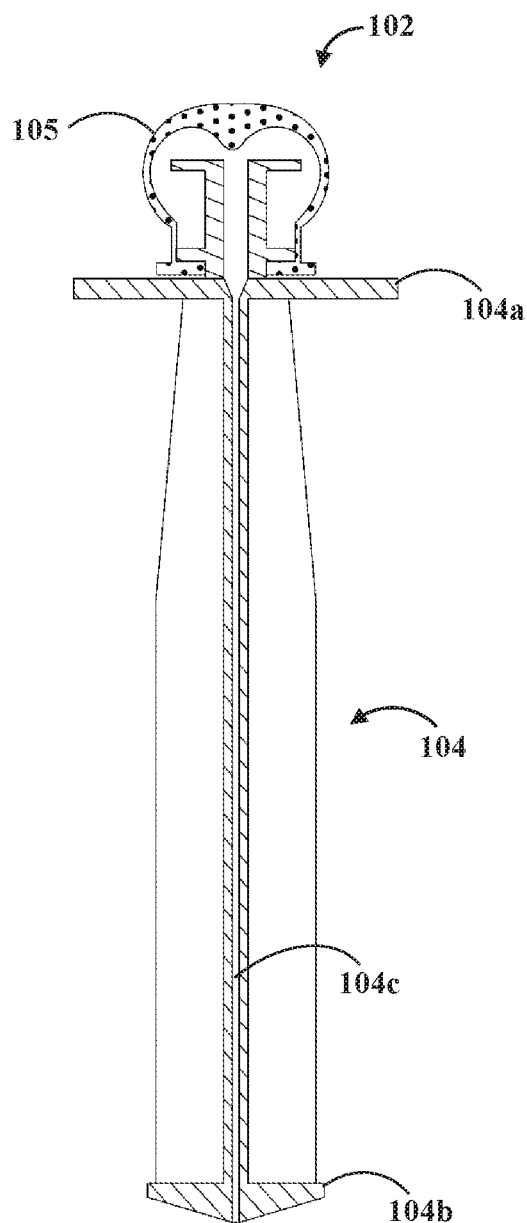
FIG. 3B exemplarily illustrates a sectional view of a plunger assembly of a dropper syringe apparatus.

FIG. 3B exemplarily illustrates a sectional view of a plunger assembly 102 of a dropper syringe apparatus 100. The plunger assembly 102 is configured to be inserted into the substantially cylindrical barrel 101, exemplarily illustrated in FIG. 3A. The plunger assembly 102 comprises a plunger shaft 104 and a flexible hollow bulb 105. The plunger shaft 104 comprises a flanged upper end 104a, a lower end 104b, and a central lumen 104c.

The plunger shaft 104 is configured to move in an upward direction and a downward direction within the substantially cylindrical barrel 101. The central lumen 104c extends from the lower end 104b to the flanged upper end 104a of the plunger shaft 104 for accommodating the fluid. The flexible hollow bulb 105 is fixedly attached to the flanged upper end 104a of the plunger shaft 104. The interior of the flexible hollow bulb 105 is in fluid communication with the central lumen 104c. The flexible hollow bulb 105 is configured to exert a pressure on the fluid accommodated within the central lumen 104c based on an external force exerted on the flexible hollow bulb 105.

Figure 3C:
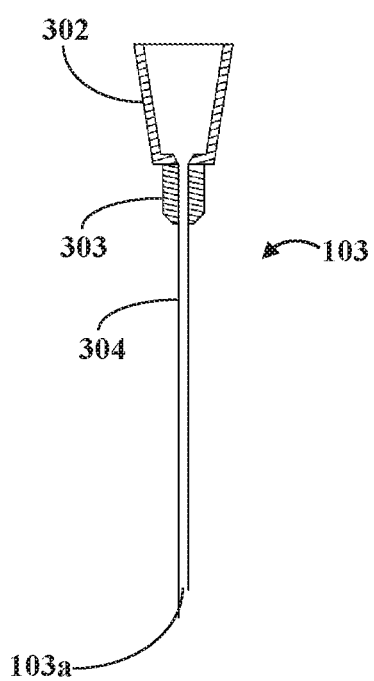
FIG. 3C exemplarily illustrates a sectional view of a needle of a dropper syringe apparatus.

FIG. 3C exemplarily illustrates a sectional view of a needle 103 of a dropper syringe apparatus 100. The needle 103 is detachably attached to the first hollow neck element 109 extending from the second opening 108 of the substantially cylindrical barrel 101 as exemplarily illustrated in FIGS. 2 and 3A. In an embodiment, a needle hole 103a is provided at the bottom of the needle 103 to dispense the sterile contents of the dropper syringe apparatus 100. The needle 103 is similar to that of a conventional syringe. The needle 103 includes a metal needle shaft 304, which is hollow and sharp, and a plastic hub 302 that is attached to the needle shaft via a narrow collar 303. The metal needle shaft has a bevel tip.

Figure 3D:
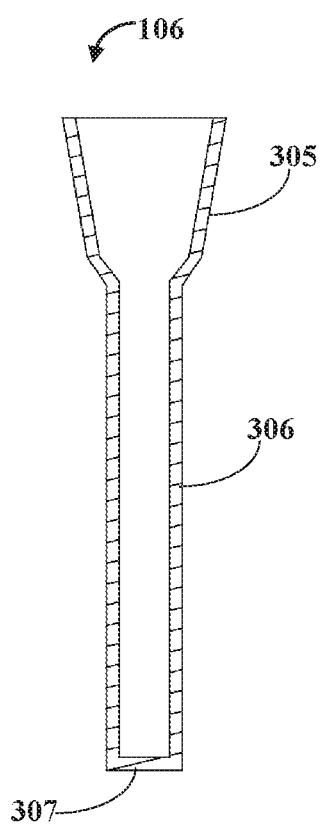
FIG. 3D exemplarily illustrates a sectional view of a needle protector of a dropper syringe apparatus.

FIG. 3D exemplarily illustrates a sectional view of a needle protector 106 of a dropper syringe apparatus 100. In an embodiment, the needle protector 106 covers the needle 103, exemplarily illustrated in FIG. 3C, of the dropper syringe apparatus 100. The needle protector 106 is similar to that of a conventional syringe. The needle protector 106 has a thick collar portion 305, a thin shaft 306, and a blind end 307. There are some prominent lines on the protector collar portion 305 and some other prominent lines on thin protector shaft to ease the manipulation of the needle protector 106 and prevent slipping.

Figure 4A:
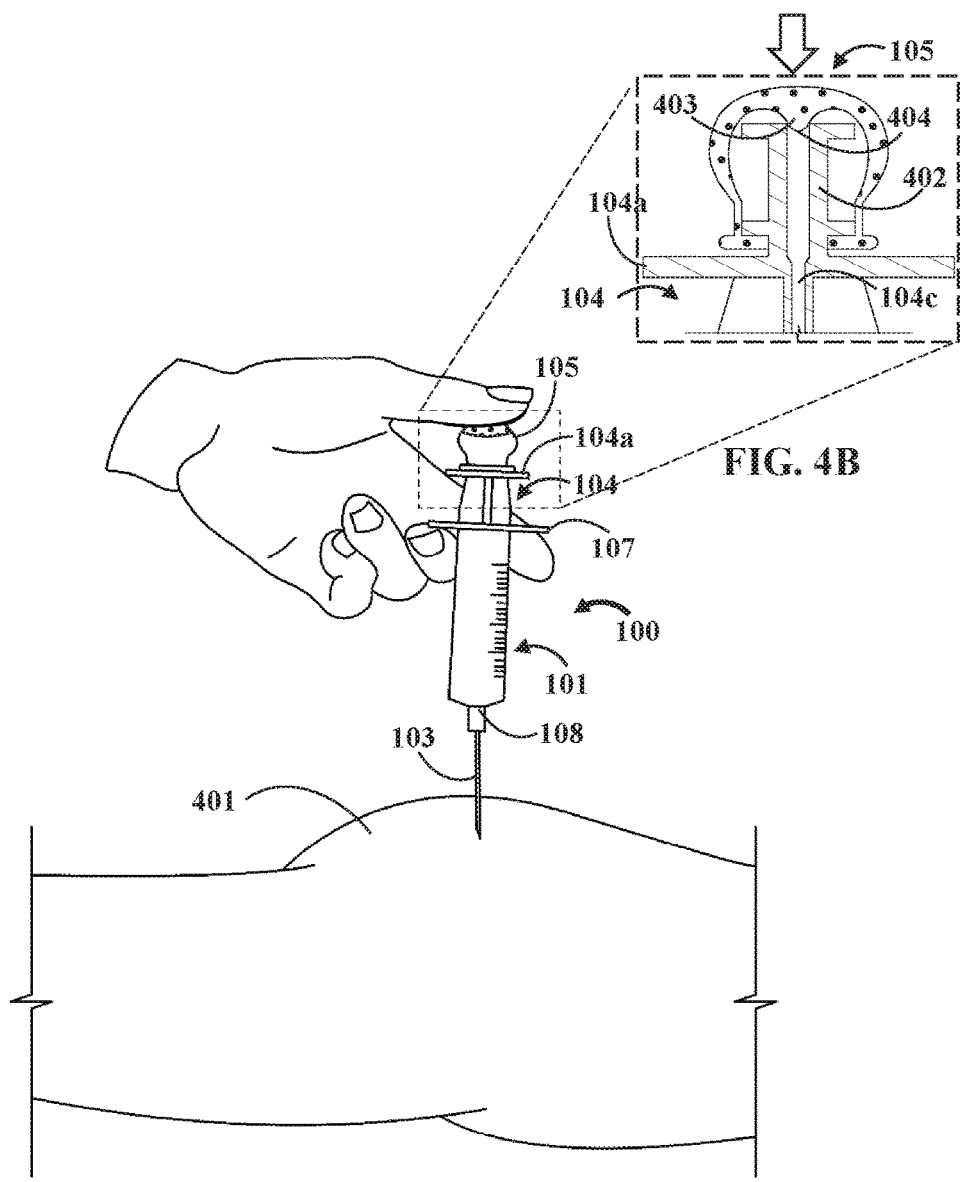
FIG. 4A exemplarily illustrates a dropper syringe apparatus while injecting the contents of the dropper syringe apparatus to an external body.

FIG. 4A exemplarily illustrates a dropper syringe apparatus 100 while injecting the contents of the dropper syringe apparatus 100 to an external body, for example, the buttocks 401 of a user. The first flanged opening 107 of the substantially cylindrical barrel 101 configured as finger grips are gripped by two fingers as exemplarily illustrated in FIG. 4A. The flanged upper end 104a of the plunger shaft 104 of the substantially cylindrical barrel 101 acts as a stop for the advancement of the plunger shaft 104 while pushing the plunger shaft 104 forward.

The pressure applied by the thumb on the flexible hollow bulb 105 is transferred to the plunger shaft 104 and causes the plunger shaft 104 to move in a downward direction. The downward movement of the plunger shaft 104 causes the contents of the dropper syringe apparatus 100 to flux out from the second opening 108. Finally, the contents of the dropper syringe apparatus 100 are injected into the buttocks 401 through the needle 103. The flexible hollow bulb portion 105 defined within the square is disclosed in the detailed description of FIG. 4B.

FIG. 4B exemplarily illustrates an enlarged sectional view of a flexible hollow bulb 105 shown in FIG. 4A. The dropper syringe apparatus 100 comprises a second hollow neck element 402 attached to the flanged upper end 104a of the plunger shaft 104. The second hollow neck element 402 is housed within the flexible hollow bulb 105 as exemplarily illustrated in FIG. 4B. The second hollow neck element 402 is in fluid communication with the central lumen 104c of the plunger shaft 104 and the flexible hollow bulb 105 to transfer fluid between the central lumen 104c and the flexible hollow bulb 105.

When a thumb is pushed on the top of the rubber flexible hollow bulb 105, an interior projection 403 of flexible hollow bulb 105 squeezes into the opening 404 of the second hollow neck element 402. Consequently, there is no way for air in the flexible hollow bulb 105 to enter the central lumen 104c of the plunger shaft 104. The pressure applied by the thumb is transferred to the plunger shaft 104 by the flanged upper end 104a of the plunger shaft 104 and causes the plunger shaft 104 to move forward. The movement of the plunger shaft 104 causes the syringe contents to flux out from the syringe end hole. Finally, the syringe contents will be injected into the external body through the needle hole 103a, exemplarily illustrated in FIGS. 2 and 3C.

Figure 5:
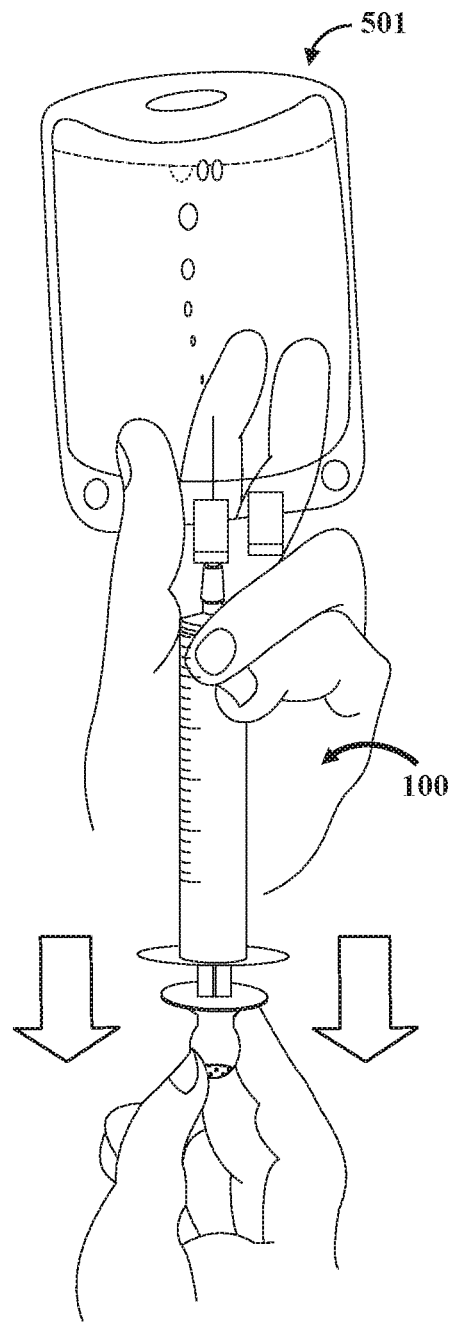
FIG. 5 exemplarily illustrates a dropper syringe apparatus extracting a sterile fluid from a sealed plastic bag.

FIG. 5 exemplarily illustrates a dropper syringe apparatus 100 extracting a sterile fluid from a sealed plastic bag 501. For example, an operator uses the dropper syringe apparatus 100 to draw out a sterile liquid from a sealed plastic bag 501. The arrows indicate the direction of the lower hand movement that cause to retract the plunger shaft and a sucking action of the dropper syringe apparatus 100.

Figure 6B:
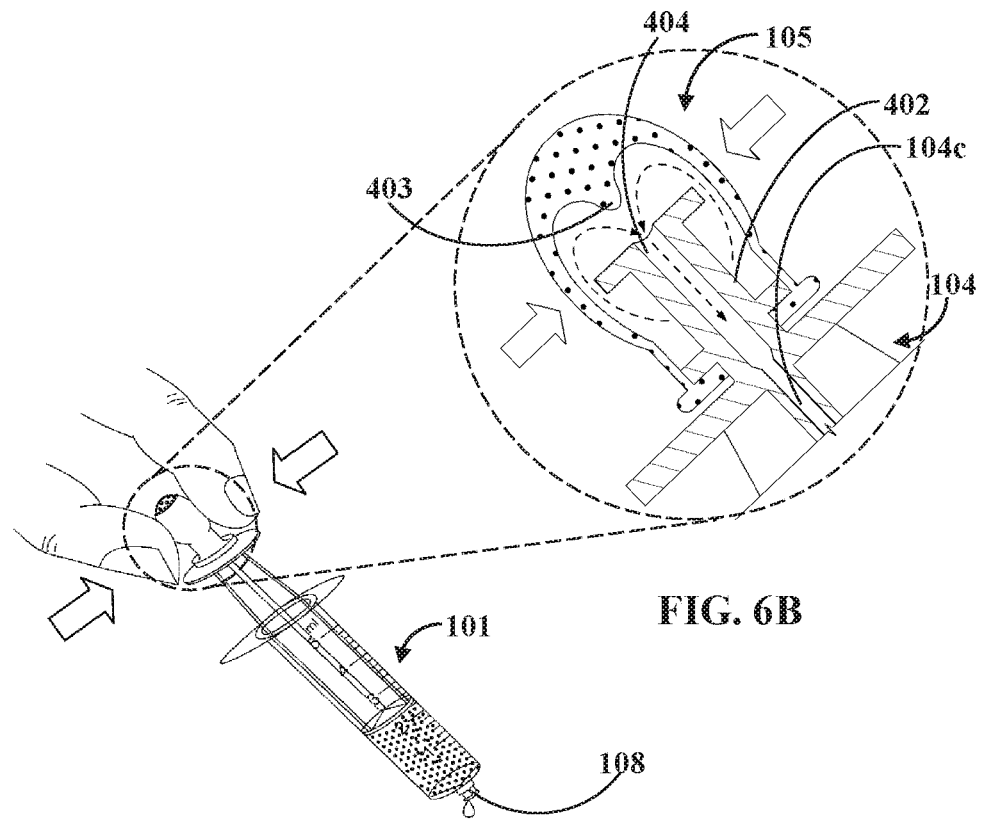
FIG. 6B exemplarily illustrates an enlarged sectional view of a portion of the dropper syringe apparatus 100 shown in FIG. 6A.
Figure 6A:
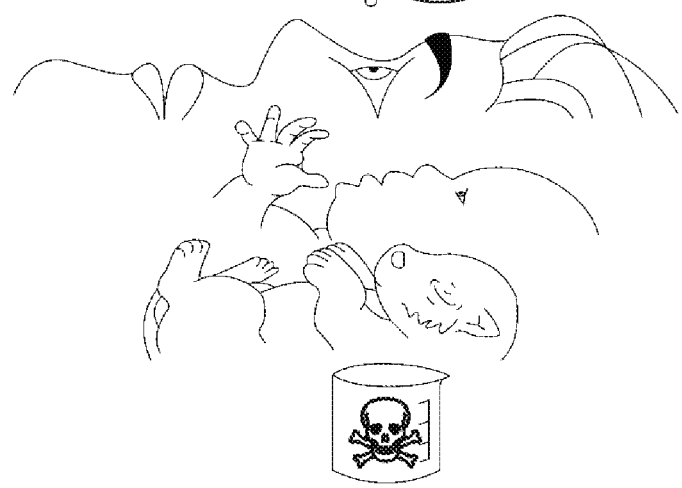
FIG. 6A exemplarily illustrates a dropper syringe apparatus used as a dropper.

FIG. 6A exemplarily illustrates a dropper syringe apparatus 100 used as a dropper. FIG. 6B exemplarily illustrates an enlarged sectional view of a portion of the dropper syringe apparatus 100 shown in FIG. 6A defined in a circle. The operator manipulating the flexible hollow bulb 105 using two fingers drops the contents of the dropper syringe apparatus 100 onto a target place (eye, mouth of a newborn, mouth of a pup or a chemistry lab beaker.) as exemplarily illustrated in FIG. 6A.

Manipulation of the flexible hollow bulb 105 using two fingers drives the air inside the flexible hollow bulb 105 into the central lumen 104c of the plunger shaft 104 as exemplarily illustrated in FIG. 6B. The air exits from the central lumen 104c and enters the substantially cylindrical barrel 101 as air bubbles. Entrance of air bubbles into the substantially cylindrical barrel 101 causes syringe contents to slowly exit off from the second opening 108 as drops. Because the flexible hollow bulb 105 is made of rubber, control of pressure applied by the fingers is much easier and the operator can instill a few drops one by one, as he/she wants. The arrow shows the directions of pressure on the flexible hollow bulb 105.

FIG. 6B exemplarily illustrates what happens when an operator manipulates the flexible hollow bulb 105 by two fingers. The interior projection 403 of flexible hollow bulb 105 moves away from the opening 404 of the second hollow neck element 402. Consequently, the air in the flexible hollow bulb 105 is driven to enter the central lumen 104c of the plunger shaft 104. The broken line arrows show the direction of airflow from the flexible hollow bulb 105 to the central lumen 104c. The arrows show the direction of pressure on the flexible hollow bulb 105.

Using the dropper syringe apparatus 100 you can draw out a sterile liquid and directly instill it as drops into an eye, an ear or nostrils in a safe and precise manner with minimum waste. The dropper syringe apparatus 100 draws out liquid from a sealed container like a syringe and then detaches its needle and manipulates its rubber flexible hollow bulb by two fingers for dropping the drops one by one like a precise dropper.

Using the dropper syringe apparatus 100 allows users to prevent wasting of liquid medications and medical fluids, but also better keeps the sterility of these liquids. Like other syringes, the dropper syringe apparatus 100 could be produced in different volumes and sterile conditions. Further, the dropper syringe apparatus 100 can be provided to public in sealed packs, first aid kits for soldiers, first aid kits for climbers, etc. Expensive ophthalmology medications could be provided in sealed vials for patients to apply by themselves using the dropper syringe apparatus 100. Moreover, the dropper syringe apparatus 100 could be used in laboratories to transfer liquid chemicals with hazardous fumes like formaldehyde and glutaraldehyde.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method.

Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A dropper syringe apparatus for drawing or dispensing fluid from or to an external body, the dropper syringe apparatus comprising:
a substantially cylindrical barrel comprising a first opening and a second opening, the second opening smaller than the first opening, wherein the first opening is flanged as two symmetrical finger grips, and wherein the substantially cylindrical barrel is configured to store the fluid;
a plunger assembly configured to be inserted into the substantially cylindrical barrel, the plunger assembly comprising:
a plunger shaft comprising a flanged upper end, a lower end, and a central lumen, the plunger shaft configured to move in an upward direction and a downward direction within the substantially cylindrical barrel, wherein the central lumen extends from the lower end to the flanged upper end of the plunger shaft for accommodating the fluid;
a flexible hollow bulb fixedly attached to the flanged upper end of the plunger shaft, wherein an interior of the flexible hollow bulb is in fluid communication with the central lumen, the flexible hollow bulb configured to exert a pressure on the fluid accommodated within the central lumen based on an external force exerted on the flexible hollow bulb;
a needle detachably attached to a first hollow neck element extending from the second opening of the substantially cylindrical barrel, the needle configured to draw or dispense the fluid from or to the external body; and
further comprising a second hollow neck element attached to the flanged upper end of the plunger shaft, the second hollow neck element housed within the flexible hollow bulb, wherein the second hollow neck element is in fluid communication with the central lumen of the plunger shaft and the flexible hollow bulb to transfer fluid between the central lumen and the flexible hollow bulb.

2. The dropper syringe apparatus of claim 1, further comprising a needle protector configured to house the needle and prevent contamination of the needle.

3. The dropper syringe apparatus of claim 1, wherein the needle is detached from the first hollow neck element and drops of the fluid are dispensed from the first hollow neck element based on the external force exerted on the flexible hollow bulb.

4. The dropper syringe apparatus of claim 1, wherein the flanged upper end of the plunger shaft is configured as a circular handle.

5. The dropper syringe apparatus of claim 1, wherein the substantially cylindrical barrel is of a transparent plastic material.

6. The dropper syringe apparatus of claim 1, wherein the flexible hollow bulb is of a rubber material.

7. The dropper syringe apparatus of claim 1, wherein the fluid is a sterile liquid.

8. The dropper syringe apparatus of claim 1, wherein the external body is one of a sealed vial storing sterile liquid, a body part of a human, and a body part of an animal.

9. A dropper syringe apparatus for drawing or dispensing fluid from or to an external body, the dropper syringe apparatus comprising:
a substantially cylindrical barrel comprising a first opening and a second opening, the second opening smaller than the first opening, wherein the first opening is flanged as two symmetrical finger grips, and wherein the substantially cylindrical barrel is configured to store the fluid;
a plunger assembly configured to be inserted into the substantially cylindrical barrel, the plunger assembly comprising:
a plunger shaft comprising a flanged upper end, a lower end, and a central lumen, the plunger shaft configured to move in an upward direction and a downward direction within the substantially cylindrical barrel, wherein the central lumen extends from the lower end to the flanged upper end of the plunger shaft for accommodating the fluid;
a second hollow neck element attached to the flanged upper end of the plunger shaft, wherein the second hollow neck element is in fluid communication with the central lumen of the plunger shaft and a flexible hollow bulb to transfer fluid between the central lumen and the flexible hollow bulb;
the flexible hollow bulb fixedly attached to the flanged upper end of the plunger shaft, wherein an interior of the flexible hollow bulb houses the second hollow neck element, wherein the flexible hollow bulb is configured to exert a pressure on the fluid accommodated within the central lumen based on an external force exerted on the flexible hollow bulb; and
a needle detachably attached to a first hollow neck element extending from the second opening of the substantially cylindrical barrel, the needle housed in a needle protector, wherein the needle is configured to draw or dispense the fluid from or to the external body.

10. The dropper syringe apparatus of claim 9, wherein the needle is detached from the first hollow neck element and drops of the fluid are dispensed from the first hollow neck element based on the external force exerted on the flexible hollow bulb.

11. The dropper syringe apparatus of claim 9, wherein the first hollow neck element comprises an upper flange and a lower flange, wherein a diameter of the upper flange is greater than a diameter of the lower flange, wherein the upper flange is configured to detachably attach the needle, and wherein the lower flange is configured to dispense the fluid drop by drop.

12. The dropper syringe apparatus of claim 9, wherein the flanged upper end of the plunger shaft is configured as a circular handle.

13. The dropper syringe apparatus of claim 9, wherein the substantially cylindrical barrel is of a transparent plastic material.

14. The dropper syringe apparatus of claim 9, wherein the flexible hollow bulb is of a rubber material.

15. The dropper syringe apparatus of claim 9, wherein the fluid is a sterile liquid.

16. The dropper syringe apparatus of claim 9, wherein the external body is one of a sealed vial storing sterile liquid, a body part of a human, and a body part of an animal.

* * * * *